(12) United States Patent
Ettema et al.

(10) Patent No.: US 7,642,353 B2
(45) Date of Patent: Jan. 5, 2010

(54) PROCESS OF MAKING CRYSTALLINE ARIPIPRAZOLE

(75) Inventors: Gerrit Jan Ettema, Nijmegen (NL); Raymond Westheim, Nijmegen (NL); Faysal Kalmoua, Oss (NL)

(73) Assignee: Synthon BV, Nijmegen (NL)

( * ) Notice: Subject to any disclaimer, the term of this patent is extended or adjusted under 35 U.S.C. 154(b) by 762 days.

(21) Appl. No.: 11/281,489

(22) Filed: Nov. 18, 2005

(65) Prior Publication Data

US 2006/0142579 A1 Jun. 29, 2006

Related U.S. Application Data

(60) Provisional application No. 60/628,653, filed on Nov. 18, 2004.

(51) Int. Cl.
*A61K 31/497* (2006.01)
*C07D 401/12* (2006.01)

(52) U.S. Cl. .................. 544/363; 514/252.13

(58) Field of Classification Search ................ 544/363; 514/252.13
See application file for complete search history.

(56) References Cited

U.S. PATENT DOCUMENTS

| 4,734,416 A | 3/1988 | Banno et al. |
| 5,006,528 A | 4/1991 | Oshiro et al. |
| 2004/0058935 A1 | 3/2004 | Bando et al. |

FOREIGN PATENT DOCUMENTS

| EP | 367141 | 1/1996 |
| WO | WO 03/026659 | 4/2003 |
| WO | WO 2005/058835 A2 | 6/2005 |

OTHER PUBLICATIONS

"Study on Crystal Transformation of Aripiprazole" The Fourth Japan-Korea Symposium on Separation Technology (1996), p. 937.

*Primary Examiner*—James O Wilson
*Assistant Examiner*—Ebenezer Sackey
(74) *Attorney, Agent, or Firm*—Mark R. Buscher

(57) ABSTRACT

Crystalline aripiprazole Form B can be formed by crystallizing from a solvent selected from 1-propanol, 2-propanol, 1-butanol, ethyl acetate, acetonitrile or a combination thereof.

22 Claims, 2 Drawing Sheets

PROCESS OF MAKING CRYSTALLINE ARIPIPRAZOLE

This application claims the benefit of priority from U.S. Provisional Application 60/628,653, filed Nov. 18, 2004, the entire contents of which are incorporated herein by reference.

BACKGROUND OF THE INVENTION

The present invention relates to processes of making crystalline 7-[4-[4-(2,3-dichlorophenyl)-1-piperazinyl]butoxy]-3,4-dihydrocarbostyril, also known as aripiprazole, to populations of crystalline particles thereof, and to pharmaceutical compositions containing the same.

Aripiprazole is a compound of the formula (1).

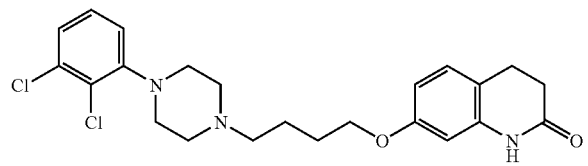

(1)

It is a commercially marketed, pharmaceutically active substance useful for treatment of schizophrenia. It is disclosed in EP 367141/U.S. Pat. No. 5,006,528. The commercially marketed product contains the compound (1) as the free base; i.e., not as an aripiprazole salt.

Solid state aripiprazole was prepared in U.S. Pat. No. 5,006,528 by a two-fold recrystallization of crude aripiprazole from ethanol resulting in colorless flake crystals having a melting point of 139-139.5° C. In an article of Aoki (Study on Crystal Transformation of Aripiprazole, The Fourth Japan-Korea Symposium on Separation Technology, p. 937 ff (1996)), this solid state form was designated as Type I aripiprazole and identified as an anhydrate. Aoki also teaches that the Type I aripiprazole may be converted into a Type II aripiprazole by heating at 130-140° C. for 15 hours. This product is an anhydrate as well with a melting point of 150° C. When both Type I and Type II aripiprazole were recrystallized from an alcoholic solvent containing water up to 20%, the product is an aripiprazole hydrate labeled as Type III by Aoki. Type III aripiprazole can be converted into Type I by heating at 80° C.

WO 03/26659 (EP 1330249) teaches that Type I aripiprazole, the alleged original solid form of aripiprazole, is significantly hygroscopic. In an effort to find a form of aripiprazole having reduced hygroscopicity and better processing qualities, seven crystalline forms (A-G) were described.

Hydrate Form A is taught as a useful intermediate for making anhydrate forms. Hydrate Form A can be prepared by milling Aoki's hydrated Type III. Contrary to the conventional Form III hydrate, the Hydrate Form A does not exhibit sharp dehydration endothermic peak at 123.5° C. at TGA, but has a gradual endothermic peak between 60-120° C.

Anhydrous Form B, which seems to be the preferred crystalline form, is not hygroscopic; i.e., less than 0.4% water uptake in 24 hours, and is a stable crystalline form. It can be prepared by heating the Hydrated Form A, preferably at 90-125° C. for 3-50 hours or by heating the Type I/Type II aripiprazole at 90-125° C. Although the Anhydrate Form B of WO 03/26659 is not hygroscopic, it suffers from being unsuitable for milling. Specifically, if milling is attempted in order to create small particle sizes such as 50 microns or less, the milled substance tends to adhere to the milling machine making an industrial process difficult. To overcome this problem, WO 03/26659 teaches forming Hydrate Form A aripiprazole, milling the Hydrate Form A to the desired size and then heat converting to Anhydrate Form B.

The other anhydrate forms disclosed therein are briefly summarized below:

Form C: Prepared by heating an aripiprazole anhydrate to 140-150° C. Endothermic peak around 150.2° C.

Form D: Prepared by recrystallization of aripiprazole anhydrate from toluene. Endothermic peaks at 136.8 and 141.6° C.

Form E: Prepared by double heating, dissolving, and crystallizing aripiprazole in acetonitrile with crystallization at about 70° C. Endothermic peak at 146.5° C.

Form F: Prepared by heating a suspension of aripiprazole anhydrate in acetone. Endothermic peaks at 137.5 and 149.8° C.

Form G: Prepared by putting glassy state of aripiprazole anhydrate in a sealed vessel and keeping it at room temperature for at least 2 weeks. Exothermic peak at 122.7° C., endothermic peak at 141.0° C.

As an anhydrous, non-hygroscopic form of aripiprazole is advantageous, it would be desirable to form such a crystalline form without the need for a heat treatment or heat conversion. In particular, it would be desirable to find an alternate, economically more advantageous process, which does not require long-term exposure to high temperatures.

SUMMARY OF THE INVENTION

The present invention is based on the discovery that Form B aripiprazole, as hereinafter defined, can be formed by crystallization from an appropriate solvent, namely 1-propanol, 2-propanol, 1-butanol, ethyl acetate, acetonitrile or combinations thereof. Accordingly, a first aspect of the present invention relates to a process, which comprises crystallizing aripiprazole Form B from a solution of aripiprazole dissolved in a solvent selected from the group consisting of 1-propanol, 2-propanol, 1-butanol, ethyl acetate, acetonitrile and mixtures thereof.

Another aspect of the invention relates to a process for making aripiprazole Form B, which comprises providing a solution which contains aripiprazole dissolved in a solvent selected from the group consisting of 1-propanol, 2-propanol, 1-butanol, ethyl acetate, acetonitrile, and combinations thereof; crystallizing the aripiprazole from the solution to form aripiprazole crystals; and recovering the crystals to obtain isolated crystalline aripiprazole Form B.

A further aspect of the invention relates to a population of crystalline aripiprazole Form B particles, wherein at least 95% of said particles have a particle size of less than 200 microns and wherein said population is substantially non-hygroscopic. Such a population is conveniently made by one of the aforementioned processes. The non-hygroscopic aripiprazole Form B population is advantageously used in a pharmaceutical composition in combination with at least one pharmaceutically acceptable excipient.

DETAILED DESCRIPTION OF THE INVENTION

Figure 1:
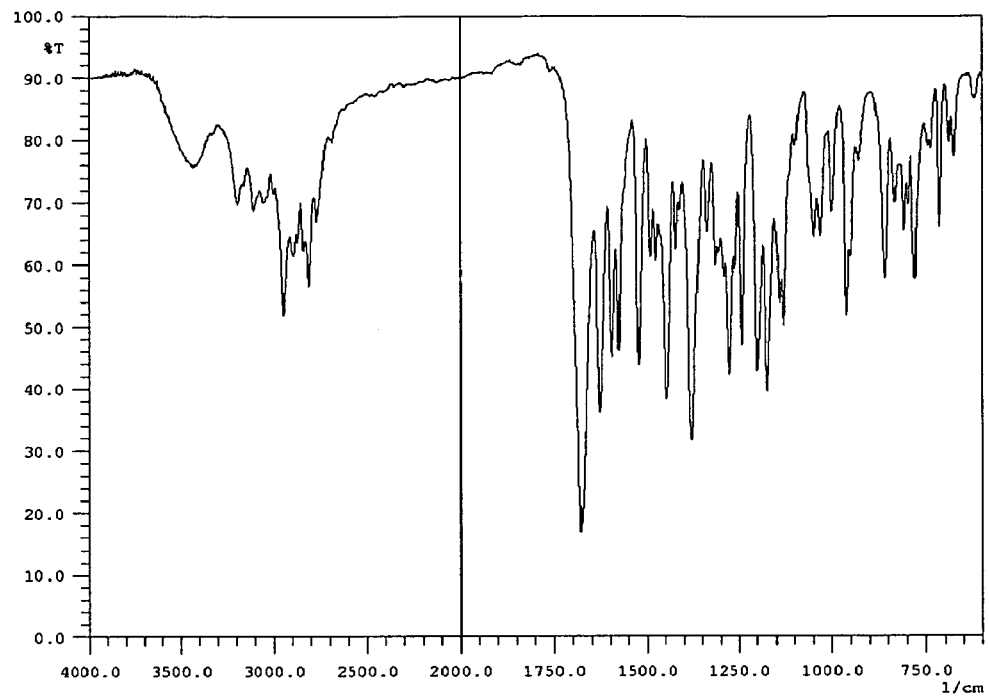
FIG. 1 represents an IR spectrum of aripiprazole Form B obtained in Example 6
Figure 2:
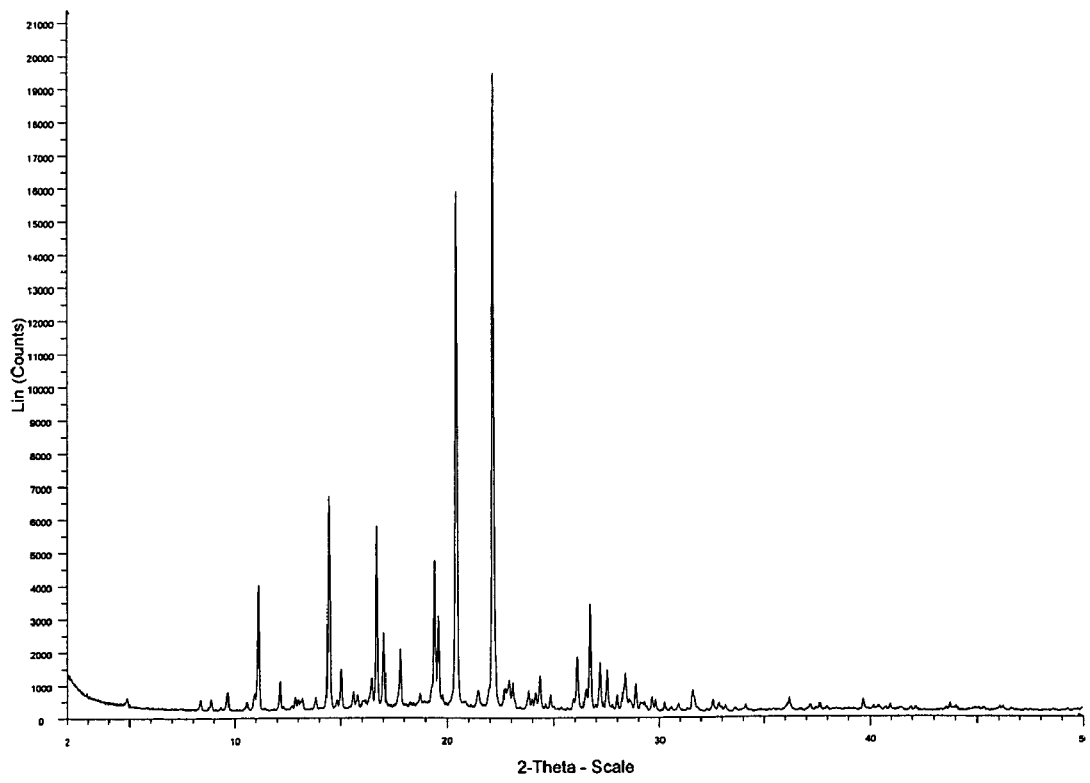
FIG. 2 represents an XRPD pattern of aripiprazole Form B obtained in Example 6.
Figure 3:
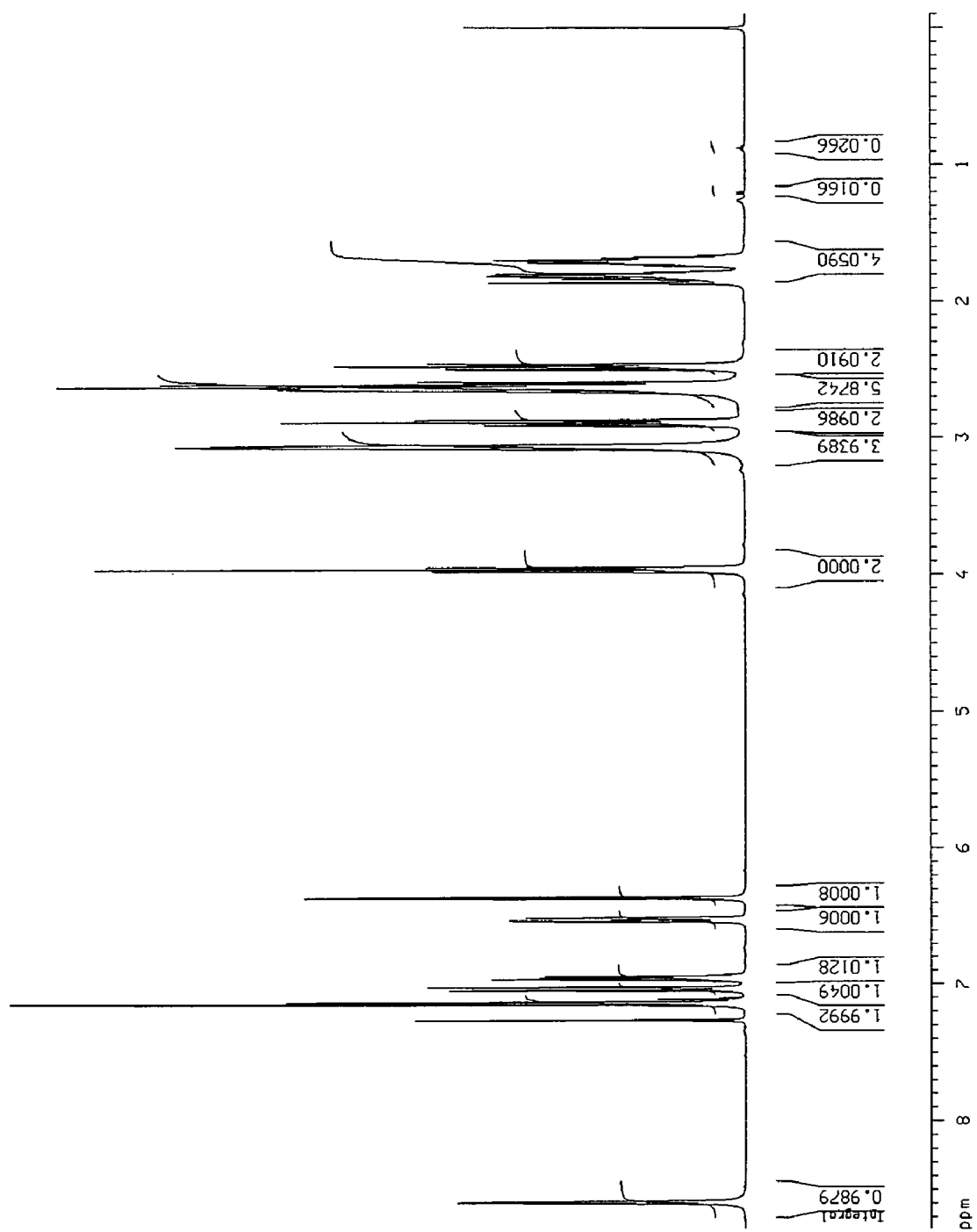
FIG. 3 represents an NMR spectrum of aripiprazole Form B obtained in Example 6.

The invention is based on a surprising finding that certain solvents, specifically 1-propanol, 2-propanol, 1-butanol, ethyl acetate, acetonitrile, or combinations thereof, can provide Form B of aripiprazole when used as solvents for crystallization. That is, Form B can be directly precipitated without the need to heat treat. Further, the Form B can be directly precipitated in a non-hygroscopic form.

As used herein "Form B" of aripiprazole means a crystalline aripiprazole substance having an x-ray powder diffraction (XRPD) pattern that substantially corresponds to the Form B product as defined in WO '659. "Substantially corresponds" is meant to cover variations/differences in the pattern that would not be understood by a worker skilled in the art to represent a difference in crystal structure, but rather differences in technique, sample preparation, impurities, etc.

Typically the Form B aripiprazole will have a single melting endotherm peak within the range of 138 to 144° C., especially 139-141° C., measured using differential thermal analysis (DTA) or differential scanning calorimetry (DSC). While in theory the values should correspond to the values recited in WO 03/26659, the DTA and DSC values should be used with a certain care as these types of data are dependant on measuring conditions such as heating rate, type of equipment, sample purity, sample loading, etc. Indeed, it is even possible for a Form B aripiprazole, as defined above, to exhibit two endothermic peaks.

The Form B aripiprazole is a relatively stable crystalline form suitable for making pharmaceutical compositions on an industrial scale. The Form B aripiprazole (in pure state, i.e. free from other forms) is anhydrous, meaning it neither contains water or other solvent bound as part of the crystal lattice. This should be distinguished from wet crystals that have water or solvent adhered thereto. Such liquid is permitted (e.g., a "wet" or damp crystalline substance), so long as it is not part of the regular repeating unit of the crystal lattice. Generally, the Form B aripiprazole is non-hygroscopic. However, it can be hygroscopic if, inter alia, it is formed in small particle sizes and/or is milled as discussed hereinafter.

The solvents used in the present invention are 1-propanol, 2-propanol, 1-butanol, ethyl acetate, acetonitrile, or combinations thereof. The ratio of components within the mixture(s) is not particularly limited. Normally the solvent is anhydrous, i.e. traces of water ordinarily present in conventional batch should be controlled and, if necessary, removed. Typically the water content within the solvent system is less than 1%. Surprisingly, the use of such solvents in crystallization can facilitate the formation of Form B crystals of aripiprazole. In contrast, for example, it was discovered during development of the present invention that alcohols such as methanol and ethanol, produce alcoholates, that is solvates of aripiprazole. While the bound solvent can be removed by heating to form Form B aripiprazole, it is more convenient to use the solvents of the present invention wherein the anhydrous/non-solvated aripiprazole crystalline material is directly formed without the need for heat treating/thermoconversion of the crystalline structure.

The crystallization of aripiprazole as Form B is carried out using 1-propanol, 2-propanol, 1-butanol, ethyl acetate, acetonitrile or combinations thereof, as the solvent in crystallization techniques generally known in the art. That is, a solution containing aripiprazole dissolved in the solvent of the invention is solidified by crystallizing the dissolved aripiprazole out of the solution. The aripiprazole-containing solution can be provided in a number of ways and is not particularly limited. For example, aripiprazole can be dissolved in the solvent or it can be synthesized in the solvent. In this regard, any form of aripiprazole may be used as the starting material; i.e., an isolated or un-isolated crude product arisen from the synthesis of aripiprazole or an aripiprazole product already crystallized such as the Type I-III or Form B-G as made by the techniques disclosed in the art, or an alcoholate such as a methanolate or a hemi-ethanolate. The latter alcoholates are more fully described in U.S. Provisional Application 60/628,654, filed Nov. 18, 2004, entitled "Crystalline Aripiprazole Solvates," the entire contents of which are incorporated herein by reference. Typically the solvent is heated in order to increase the solubility of the aripiprazole. This includes forming a suspension of aripiprazole in the solvent and then heating until the solid dissolves or, alternatively, adding aripiprazole gradually into the already heated or hot solvent. A "hot" solvent has a temperature within the range of its boiling point to 20° C. less than its boiling point, typically from the boiling point to 10-15° C. below the boiling point of the solvent.

The concentration of aripiprazole in the solvent depends on the nature of solvent as well as the presence or absence of other dissolved or suspended components, e.g., reactants, side-products, etc. In general, the upper limit is the maximum concentration; i.e., the saturation concentration, at the boiling point of the solvent. Typically the concentration is at least about 20 to 250 mg/ml.

Once the solution containing aripiprazole has been provided, crystallization can be carried out by any convenient method. Generally, the crystallization involves cooling the solution, adding a seeding crystal(s), and/or combining with a contrasolvent.

In a first variant of the process, the hot solution of aripiprazole is subjected to cooling, preferably under stirring. The rate of cooling is not particularly limited and in general, it may affect the particle size of the formed crystals. A quicker rate of cooling generally leads to smaller crystals. A preferred cooling rate is spontaneous cooling; i.e., allowing the solution to cool without special cooling or heating measures. Indeed, when using acetonitrile as a solvent, the Form B can be obtained under spontaneous cooling of a hot solution, such as a concentration of 1 gram of aripiprazole in approximately 25 ml of acetonitrile. In contrast, crystallization from acetonitrile at a temperature of about 70° C. should be avoided as the WO '659 teaches in Example 14 therein that the Form E is likely obtained.

The final temperature after cooling may also affect the particle size, the yield and/or the purity of the product. Generally the final temperature is from 0° C. to 25° C.

In a second variant, the hot solution of aripiprazole in the solvent is combined with a contrasolvent, i.e. with a liquid in which aripiprazole is insoluble or only slightly soluble. The contrasolvent may be added to the hot aripiprazole solution or vice versa, preferably under stirring. Generally, the contrasolvent is of ambient temperature or less. A suitable contrasolvent is an aliphatic hydrocarbon, e.g. hexane, heptane, etc. The amount of the contrasolvent is not particularly limited. The resulting suspension may be optionally cooled, preferably to a temperature from 0° C. to 25° C.

In both variants, the crystallization process may be induced or aided by adding small amounts of seed crystals of aripiprazole Form B. The conditions of crystallization (concentration, cooling rate) are advantageously adjusted in such a way that aripiprazole crystallizes out of the solution at a temperature less than 65° C.

As a result of crystallizing from the solvents of the invention, it is believed that aripiprazole Form B is easily and directly obtained. To confirm that the crystals are Form B, the crystals are isolated from the remaining solvent/solution and subjected to XRPD. The isolating of the crystals can be carried out by any conventional methods. In general, the solid crystalline material is recovered from the liquid portion such as by filtration or centrifugation, optionally washed such as with the solvent used or with the contrasolvent, and generally, though not necessarily, dried. The drying can be conducted in vacuo, with or with applying heat. It is an advantage of the process that the solvent may be removed without any long-term or high-temperature drying. The drying temperature advantageously does not exceed 60° C. and preferably does not exceed 40° C. Again, it is believed that the isolated wet crystals as well as the dried crystals are aripiprazole Form B.

The process of the present invention may be used for conversion of an undesired Form of aripiprazole into Form B, or for a purification of the insufficiently pure Form B. It is an advantage of the process that most of the impurities present in a crude starting material are well removed within the crystallization process of the present invention. The purification effect may be enhanced by using a surface active material prior to subjecting the aripiprazole solution to crystallization, as such material may adsorb various impurities on its surface. Any conventional material, for instance activated carbon, Hyflo etc., may be used for this purpose. After treatment of the aripiprazole solution with such material, the material is normally removed such as by filtration, before carrying out crystallization. Thus, the process of the invention may be used to make essentially pure Form B of aripiprazole, i.e., essentially free from other forms of aripiprazole and/or from structurally related impurities. The essentially pure aripiprazole Form B comprises more than 98% of the Form B.

If the particle size distribution obtained as a result of the process of the invention is insufficient for the intended purpose, e.g., the dissolution profile, bioavailability of the aripiprazole, etc., is not within a desired range, then sieving of the crystal particles can be used to modify the population. As was described in WO 03/26659, milling of Form B aripiprazole leads to unsatisfactory results. In addition to the clumping described in the prior art, it has now been observed that milling may tend to introduce non-crystalline modifications to the material. Such amorphous substance is undesired due to clumping and also increases hygroscopicity and reduces dissolution. Indeed, it has been found with surprise that milling, which brings the product into contact with significant energy, considerably decreases the solubility profile of the product, e.g., in pharmaceutical applications. It is theorized, without wishing to be bound, that it could be that the energy causes an amorphization process and the presence of a certain amount of an amorphous (non-crystalline) aripiprazole causes the differences in solubility. Moreover, it has been discovered that aripiprazole Form B of very small particle size appears also to be hydrophobic. Thus, the population of aripiprazole Form B particles should not be too large or too small. In general, the population should contain at least 95% of particles having a particle size less than 200 microns. On the other hand, it is generally advantageous that less than 20% of particles should have a particle size of 10 microns or less. In some embodiments, the average particle size is between 40 and 50 microns. Other embodiments provide at least 95%, more typically about 100%, of the particles having a size within the range of 40-200 microns, more typically 50-200 microns. The desired population can be obtained by sieving with one or more sieves. Unlike milling, the sieving process does not bring significant energy to bear on the aripiprazole crystalline material and the crystalline form is not usual adversely affected by the process.

This surprising fact relates not only to the aripiprazole Form B prepared by the process of the present invention, but also to the Form B prepared by methods of the prior art or any other process. Thus, a process of improving or adjusting particle size of aripiprazole Form B, characterized in that the aripiprazole Form B is subjected to sieving through a sieve of the desired mesh screen, is another aspect of the present invention. Advantageously, the desired fraction is obtained by using two sieves with mesh sizes of a selected upper and lower limit, and fractions having particle sizes below and above the limits are discarded or reprocessed.

Aripiprazole Form B, sieved through a sieve of the mesh size of less than 200 microns, preferably through sieves of mesh sizes between 50 and 200 microns (=a population of particles of Aripiprazole Form B, wherein more than 95% of particles have a particle size between 50 and 200 microns), is a preferred product as it has improved manufacturing and dissolution characteristics, particularly in making pharmaceutical tablets.

The aripiprazole Form B can be formulated into a pharmaceutical composition, especially a tablet or capsule, by combining the same with one or more pharmaceutically acceptable excipients. Generally the amount of aripiprazole is within the range of 1 to 50 mg per unit dose, and specially 2, 5, 10, 15, 20, 25, or 30 mg per tablet.

The present invention is more particularly described and explained by the following examples. It is to be understood, however, that the present invention is not limited to these examples and various changes and modifications may be made without departing from the scope of the present invention.

EXAMPLES

Reference Example

Form B Aripiprazole According to Reference Example 2 of WO 03/026659

5.0 g of aripiprazole was dissolved in 100 ml of ethanol/water (4:1 V/V) at reflux. Reflux was maintained for 1 hour, while the solution was stirred with a magnetic stirrer. The hot solution was slowly cooled to room temperature taking about 1.5 hours. Crystallization already started after 30 minutes. The suspension was stirred at 0° C. for 1 hour. The crystals were isolated by filtration over a P3-glass filter (reduced pressure). The wet crystals were dried at 80° C. for 40 hours. A white, crystalline powder was obtained.

DSC: single melting peak around 138-140° C.
TGA: no mass loss up to 220° C.
XRPD: Corresponds to the XRPD spectrum of Form B as reported in WO 03/026659.
HSM: parallelepiped-like rods Example 1

1.0 g of aripiprazole was dissolved in 10 ml of ethyl acetate at reflux. To the hot solution, 5-10 mg of Form B aripiprazole was added as seed. Then, the hot solution was allowed to cool to room temperature, during which rapid crystallization occurred. The crystals were isolated by filtration over a P3-glass filter (reduced pressure) and air dried at room temperature for 3 days. White crystals (plates-like/flake-like) with a yield of 800 mg were obtained.

DSC: Single melting peak around 139-141° C. No other thermal effects could be observed.

XRPD: Corresponds to form B.

HSM: Crystal sizes are between 50-500 μm, mostly between 200-300 μm.

Example 2

1.0 g of aripiprazole was dissolved in 16 ml of 2-propanol at reflux. To the hot solution, 5-10 mg of Form B aripiprazole was added as seed. Then, the hot solution was allowed to cool to room temperature, during which crystallization occurred. Crystallization progressed slower than in Example 1. The crystals were isolated by filtration over a P3-glass filter (reduced pressure) and air dried at room temperature for 3 days. A white, crystalline powder with a yield of 850 mg was obtained.

XRPD: Corresponds to form B.

HSM: Aggregates or agglomerates of thick plates or prisms. Easy to separate crystals of 150 μm or smaller.

Example 3

2.5 g of aripiprazole and 40 ml of 2-propanol were mixed together. The suspension was stirred and heated to reflux (jacket temperature $T_j$=90° C.) and maintained at reflux for about 30 minutes. A clear solution was obtained. The solution was slowly cooled to a reaction temperature ($T_r$) of 25° C. within 1 hour under stirring. At about $T_j$=39° C. and $T_r$=41° C., crystallization started. After cooling, the suspension was stirred for an additional 50 minutes at $T_r$=25° C. Then, the crystals were isolated by filtration over a P3-glass filter (reduced pressure) and air dried overnight at room temperature. A white, crystalline powder with a yield of 2.16 g was obtained.

IR: Form B.

XRPD: Form B, no indications for any other forms.

HSM: agglomerates of rod-like or plate-like crystals. Particle size of the agglomerates is typically between 70-160 μm. When milled, small and irregular crystal fragments are obtained (<70 μm).

Example 4

110 g of aripiprazole was suspended in 1200 ml of ethyl acetate. The suspension was stirred and heated to reflux. Reflux was maintained for 15 minutes and 90 ml of ethyl acetate was evaporated off by using a Dean-Stark apparatus. The solution was allowed to cool down, at 63° C., during which crystallization started. The suspension was cooled to 25° C. in 30 minutes. The solid was collected by filtration on a glass filter (vacuum) and dried in a vacuum oven at 40° C. for 3 hours. Shiny, colorless and plate-like crystals with a yield of 98 g were obtained.

IR: Form B.

XRPD: corresponds to Form B. No indications of any other forms.

HSM: flat, prism-like and often well defined plates. The particle size of the crystals is typically between 100-700 μm. When milled, small and irregular crystal fragments are obtained (10-70 μm). These particles are opalescent, probably due to cracks and defects.

Example 5

2.0 g of aripiprazole was suspended in 32 ml of 2-propanol. The suspension was stirred and heated to reflux. Reflux was maintained for 5 minutes. The hot solution was removed from the oil bath. To the hot solution, 26 ml of n-heptane was added, the temperature dropped to about 50° C. After about 1 minute, crystallization started. The suspension was allowed to cool to room temperature. The solid was collected by filtration on a glass filter (vacuum) and air dried overnight at ambient conditions.

XRPD: corresponds to Form B, no indications of traces of another form.

HSM: (long) plates and rods, often prism-like or parallelepiped-like. Many crystals have a length of more than 100 μm.

Example 6

20.01 g of aripiprazole was suspended in 320 ml of 2-propanol. The suspension was stirred and heated to reflux. Reflux was maintained for 15 minutes. The clear hot solution was removed from the oil bath. The hot solution was slowly added to 500 ml of cold n-heptane of 0° C., stirred in an ice-water bath at 200 rpm. During addition, a white suspension was formed and the temperature rose to 20° C. The suspension was stirred at 0° C. for 15 minutes during which the temperature slowly dropped to 5° C. The solid was collected by filtration on a glass filter (vacuum) and dried overnight at 40° C. and under vacuum. A white, fluffy powder with soft lumps was obtained. The yield was 17.76 g.

IR: Form B.

XRPD: Corresponds to Form B, no indications for any traces of another form.

HSM: loose aggregates (20-70 μm) of irregular small plates. When milled gently, small (irregular) plates with a particle size between 5-50 μm can be observed.

Example 7

8.0 g of aripiprazole and 40 ml of n-butanol were mixed together. The suspension was stirred and heated to reflux and maintained at reflux for about 15 minutes. The solution was slowly cooled with 1° C./min to 25° C. (stirring continued). At about 46° C., fast crystallization occurred in less than 5 minutes. After cooling, the crystals were isolated by filtration over a P3-glass filter (reduced pressure) and dried overnight at 40° C. and under vacuum. A white and crystalline powder with a yield of 7.07 g was obtained.

DSC: Single melting peak around 139-140° C. No other effects visible.

XRPD: Corresponds to Form B

HSM: Agglomerates of plate-like crystals. The particle size is typically between 80-200 μm. There are also some isolated crystals (plates) with a crystal size of 50 μm or less.

Example 8

1.0 g of aripiprazole was dissolved in 25 ml of acetonitrile at reflux. Reflux was maintained for a few minutes. The hot solution was allowed to cool to room temperature spontaneously. During cooling, a few mg of Form B crystals were added as seed. Rapid crystallization occurred within a few minutes. The suspension was held at R.T. for about 15 minutes. Then, the crystals were isolated by filtration over a P3-glass filter (reduced pressure) and air dried overnight at R.T. Shiny crystals with a yield of 850 mg were obtained.
DSC: Single, sharp melting peak around 138-140° C.
IR: Corresponds to the IR spectrum of Form B
XRPD: Corresponds to the XRPD spectrum of Form B.

Each of the patents and journal articles mentioned above are incorporated herein by reference. The invention having been described it will be obvious that the same may be varied in many ways and all such modifications are contemplated as being within the scope of the invention as defined by the following claims.

We claim:

1. A process, which comprises:
    crystallizing aripiprazole Form B from a solution of aripiprazole dissolved in a solvent selected from the group consisting of 1-propanol, 2-propanol, 1-butanol, ethyl acetate, acetonitrile, and mixtures thereof.

2. The process according to claim 1, wherein said solvent is 2-propanol or ethyl acetate.

3. The process according to 1, wherein the solvent has a water content of less than 1%.

4. A process for making aripiprazole Form B, which comprises:
    providing a solution which contains aripiprazole dissolved in a solvent selected from the group consisting of 1-propanol, 2-propanol, 1-butanol, ethyl acetate, acetonitrile, and combinations thereof;
    crystallizing said aripiprazole from said solution to form aripiprazole crystals; and recovering the crystals from the solvent to obtain isolated crystalline aripiprazole Form B.

5. The process according to claim 4, wherein said providing step comprises forming said solution as part of a synthesizing route to make aripiprazole.

6. The process according to claim 4, wherein said providing step comprises dissolving aripiprazole in said solvent to form said solution.

7. The process according to claim 4, wherein said solvent is 2-propanol or ethyl acetate.

8. The process according to claim 4, wherein said crystallizing comprises cooling said solution.

9. The process according to claim 8, wherein said crystallizing comprises adding a seeding crystal of aripiprazole Form B.

10. The process according to claim 4, wherein said crystallizing comprises combining said solution with a contrasolvent.

11. The process according to claim 10, wherein said contrasolvent is heptane.

12. The process according to claim 4, wherein said crystallizing step uses a temperature of crystallization of 65° C. or less.

13. The process according to claim 4, wherein said recovering step comprises separating said crystals from said solvent by filtration and drying said separated crystals.

14. The process according to claim 13, wherein said drying is carried out at a temperature of 40° C. or less.

15. The process according to claim 4, which further comprises sieving said crystalline aripiprazole form B to obtain a desired particle size distribution.

16. The process according to claim 15, wherein said sieving comprises removing large particles by passing said crystalline aripiprazole Form B though a sieve having a mesh size of 200 microns.

17. The process according to claim 16, wherein said sieving further comprises removing small particles by passing said crystalline aripiprazole Form B through a sieve having a mesh size of 50 microns.

18. A population of crystalline aripiprazole Form B particles made by the process of claim 17.

19. A population of crystalline aripiprazole Form B particles, wherein at least 95% of said particles have a particle size of less than 200 microns and less than 20% of said particles have a particle size of 10 microns and less, and wherein said population is substantially non-hygroscopic.

20. A pharmaceutical composition comprising the non-hygroscopic aripiprazole Form B particle population according to claim 19 and at least one pharmaceutically acceptable excipient.

21. The process according to claim 1, wherein aripiprazole Form B seeding crystals are present during said crystallizing step.

22. The process according to claim 21, which further comprises isolating said crystalline aripiprazole Form B from said solvent.

* * * * *